(12) United States Patent
Morello et al.

(10) Patent No.: US 8,507,894 B2
(45) Date of Patent: Aug. 13, 2013

(54) CONTROL AND READOUT OF ELECTRON OR HOLE SPIN

(75) Inventors: Andrea Morello, Surry Hills (AU); Andrew Dzurak, Darlinghurst (AU); Hans-Gregor Huebl, Munich (DE); Robert Graham Clark, Balgowlah Heights (AU); Laurens Henry Willems Van Beveren, Sydney (AU); Lloyd Christopher Leonard Hollenberg, Camberwell (AU); David Normal Jamieson, Eltham (AU); Christopher Escott, Randwick (AU)

(73) Assignee: Qucor Pty Limited, Sydney, New South Wales (AU)

( * ) Notice: Subject to any disclaimer, the term of this patent is extended or adjusted under 35 U.S.C. 154(b) by 17 days.

(21) Appl. No.: 12/867,011

(22) PCT Filed: Feb. 11, 2009

(86) PCT No.: PCT/AU2009/000155
§ 371 (c)(1),
(2), (4) Date: Feb. 8, 2011

(87) PCT Pub. No.: WO2009/100483
PCT Pub. Date: Aug. 20, 2009

(65) Prior Publication Data
US 2011/0121895 A1 May 26, 2011

(30) Foreign Application Priority Data
Feb. 11, 2008 (AU) ................ 2008900616

(51) Int. Cl.
*H01L 29/06* (2006.01)
(52) U.S. Cl.
USPC .......... 257/30; 438/2; 438/104; 438/197; 438/287; 438/783; 257/324; 257/411; 257/59; 257/300; 257/406; 257/14; 257/350; 257/651

(58) Field of Classification Search
USPC .......... 257/30, 324, 411, 59, 300, 406, 14, 257/350, 651; 438/2, 104, 5, 197, 288, 38, 438/287, 783, 59
See application file for complete search history.

(56) References Cited

U.S. PATENT DOCUMENTS 6,597,010 B2 * 7/2003 Eriksson et al. ............. 257/14
6,653,653 B2 * 11/2003 Brousseau, III ............. 257/39

(Continued)

*Primary Examiner* — Fernando L Toledo
*Assistant Examiner* — Mohammed Shamsuzzaman
(74) *Attorney, Agent, or Firm* — Wood, Phillips, Katz, Clark & Mortimer (57) ABSTRACT

This invention concerns an electronic device for the control and readout of the electron or hole spin of a single dopant in silicon. The device comprises a silicon substrate in which there are one or more ohmic contact regions. An insulating region on top of the substrate. First and second barrier gates spaced apart to isolate a small region of charges to form an island of a Single Electron Transistor (SET). A third gate over-lying both the first and second barrier gates, but insulated from them, the third gate being able to generate a gate-induced charge layer (GICL) in the beneath it. A fourth gate in close proximity to a single dopant atom, the dopant atom being encapsulated in the substrate outside the region of the GICL but close enough to allow spin-dependent charge tunnelling between the dopant atom and the SET island under the control of gate potentials, mainly the fourth gate. In use either the third or fourth gate also serve as an Electron Spin Resonance (ESR) line to control the spin of the single electron or hole of the dopant atom. In a further aspect it concerns a method for using the device.

5 Claims, 8 Drawing Sheets

(56) References Cited

U.S. PATENT DOCUMENTS

| | | | |
|---|---|---|---|
| 6,744,065 B1* | 6/2004 | Samuelson et al. | 257/14 |
| 6,784,082 B2* | 8/2004 | Brousseau, III | 438/584 |
| 7,176,066 B2* | 2/2007 | Brenner et al. | 438/142 |
| 7,479,652 B2* | 1/2009 | Greentree et al. | 257/34 |
| 2003/0025133 A1* | 2/2003 | Brousseau, III | 257/213 |
| 2004/0002195 A1* | 1/2004 | Brousseau, III | 438/301 |
| 2004/0183064 A1* | 9/2004 | Samuelson et al. | 257/14 |
| 2005/0230713 A1* | 10/2005 | Brousseau | 257/213 |
| 2006/0220000 A1* | 10/2006 | Bennett et al. | 257/14 |
| 2008/0185576 A1* | 8/2008 | Hollenberg et al. | 257/14 |
| 2009/0146222 A1* | 6/2009 | Agrawal | 257/401 |
| 2010/0085678 A1* | 4/2010 | Jefferson et al. | 361/225 |

* cited by examiner

CONTROL AND READOUT OF ELECTRON OR HOLE SPIN

TECHNICAL FIELD

This invention concerns an electronic device for the control and readout of the electron or hole spin of a single dopant in silicon. In a further aspect it concerns a method for using the device.

BACKGROUND ART

On the roadmap towards building a scalable, silicon-based quantum computer, several essential milestones have already been achieved. Most importantly: The development of a single-ion implantation technology that allows the precise placement of individual phosphorus atoms in silicon [1]; The application of advanced nanofabrication, microwave and low-temperature techniques to the production and characterization of Single Electron Transistors (rf-SETs), with a charge sensitivity close to the quantum limit [2]; The control and detection of single electron transfers between individual phosphorus donors [3], obtained by combining the single-ion implantation and SET techniques; and, The layout of quantum device structures for universal fault-tolerant quantum computation and the subsequent analysis of the error threshold [4,5].

In addition, the ability to locally apply strong microwave fields to the dopants in the channel of a small MOSFET, and detect the driven electron spin transitions by Electrically Detected Magnetic Resonance (EDMR) has been recently demonstrated [6].

The prior art will now be described in greater detail with reference to FIGS. 1, 2 and 3.

MOS-Based Silicon Quantum Dot and Rf-SET

Figure 1A:
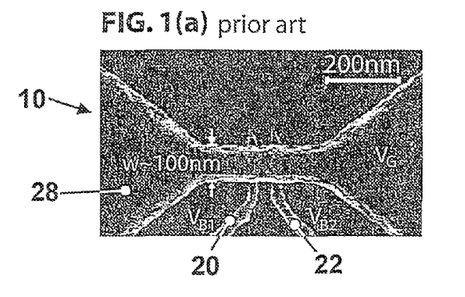
FIG. 1(a) is a scanning electron microscope (SEM) image of the dot.
Figure 1B:
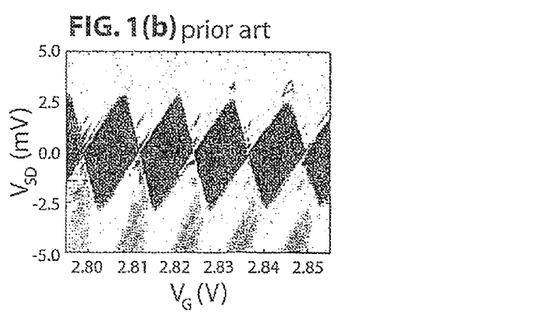
FIG. 1(b) is the bias spectroscopy of the dot.
Figure 1C:
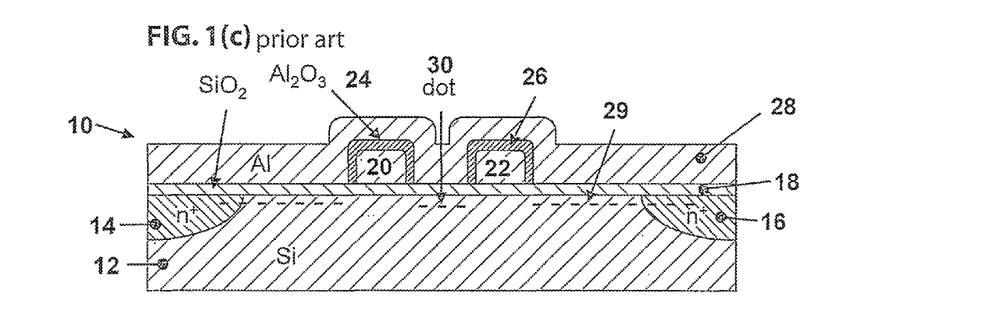
FIG. 1(c) is a schematic cross-section of the device.

Referring first to FIG. 1(a) and (c), the MOS-based silicon quantum dot structure 10 comprises a near intrinsic, high resistivity, silicon substrate 12. At either side of the device are regions 14 and 16 of phosphorus-diffused n+ areas, which provide ohmic contact to the device. A 5 nm thick layer of $SiO_2$ 18 is thermally grown on the surface. On top of this insulating oxide layer 18 two barrier gates 20 and 22 are fabricated using electron beam lithography (EBL), thermal evaporation of metal and liftoff. Each of the barrier gates 20 and 22 is ~30 nm wide, and the separation between them is less than 40 nm. The barrier gates are partially oxidized using an oxygen plasma to create insulating layers 24 and 26 over their surfaces that are a few nanometers thick.

A top gate 28 is aligned to the barrier gates 20 and 22 during a second EBL stage, and again thermally evaporated and lifted off. The top gate 28 has a narrow neck region where it crosses over the top of the two lower gates 20 and 22; seen only in FIG. 1(a).

The top gate 28 is positively biased to create a gate-induced charge layer (GICL) 29, underneath the $SiO_2$ layer 18; the n+-doped regions provide the charge for the accumulation layer. By further lowering the potential of the barrier gates, we isolate the small portion of GICL between the gates and obtain a quantum dot 30, whose coupling to the leads can be easily tuned by barrier gates 20 and 22 [7]. An example of bias spectroscopy of a single quantum dot is shown in FIG. 1(b).

Such a dot has a large charging energy and can be used as an rf-SET when connected to a resonant LC tank circuit. In this mode, a not yet fully optimized SET achieved a charge sensitivity of order 10 $\mu e/(Hz)^{1/2}$ [8], which equals or surpasses that of typical aluminium SETs [2]. This exceptional charge sensitivity enables measurement of a charge transfer equivalent to 1% of an electron, with a measurement time of 10 μs.

Figure 1D:
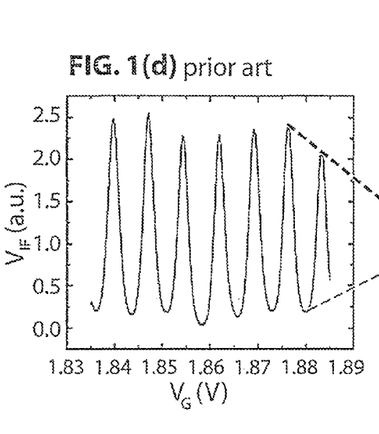
FIG. 1(d) is the conductance of the SET as a function of the voltage on the top gate.
Figure 1E:
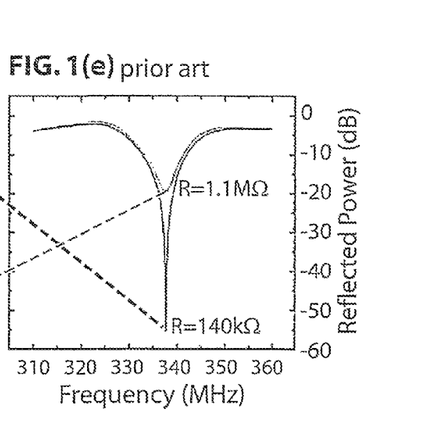
FIG. 1(e) is the rf response of the tank circuit for two different bias points of the SET, and indicated by the dashed lines.

When the device is inserted in a tank circuit, Coulomb blockade peaks FIG. 1(d) are obtained from the modulation of the reflected microwave power, see FIG. 1(e), when changing the potential of the top gate. The charge sensitivity achieved by biasing the device on the steepest slope of the Coulomb peaks is better than 10 $\mu e/(Hz)^{1/2}$ [7,8].

The Si-SET has several important advantages, as compared to the more common Al-SETs. First, its fabrication is entirely MOS-compatible, since it does not require double-angle evaporation. Second, the thin (and nontunable) $Al_2O_3$ tunnel junctions—are replaced by tuneable barriers controlled by the gate potentials; this also reduces the vulnerability of the device due to uncontrolled or random electrostatic charges. Third, the Si-SET does not suffer from the difficulty of operating in magnetic fields of order 1 T, where Al-SETs undergo a transition from superconducting to normal state. Fourth, Si-SETs are immune to most of the charge offset noise that afflicts Al-SET devices [9].

Transport by Resonant Tunneling Through Single Dopants

Figure 2:
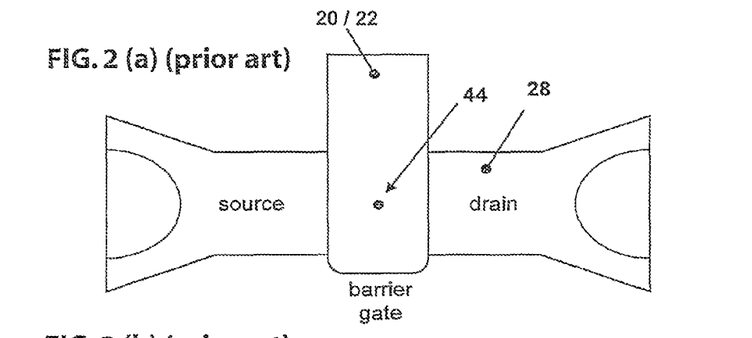
FIG. 2 illustrates a single barrier accumulation layer device with a dopant in the barrier.
Figure 3A:
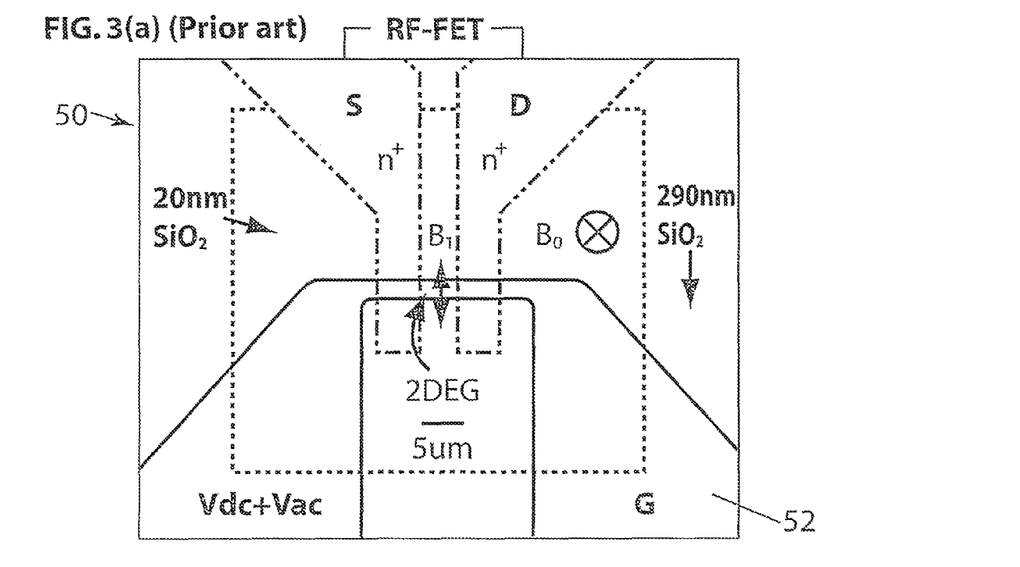
FIG. 3(a) is a SEM image of the device.

The simplest structure we can devise to study individual dopants with the MOS-based structures described above, is a single tunnel barrier 20/22 interrupting a GICL 29, with a single dopant 44 implanted underneath the barrier gate, as sketched in FIG. 2. This device can be thought of as "half" of the Si quantum dot of FIG. 1, with the addition of a dopant under the barrier gate.

While varying the height of the tunnelling barrier for the charges, the barrier gate also has the function of bringing the dopant level in resonance with the Fermi level $E_F$ of the leads, see FIG. 2(c). In the presence of a magnetic field, the Zeeman-split dopant states can also be resolved. By applying a small source-drain bias and tuning the dopant level at resonance with the Fermi energies of the GICL, we expect to observe a very sharp conductivity peak, as recently demonstrated in similar experiments on finFETs [10] and Schottky devices [11]. A first observation of such conductivity peaks in this type of devices is shown in FIG. 2(d).

By inducing a Zeeman splitting of the electron or hole spin states ("spin down" 64, $|\downarrow\rangle$), and "spin up" 66, $|\uparrow\rangle$) with an external magnetic field, we can also demonstrate spin-dependent tunnelling, see FIG. 2(c), which is an essential ingredient for the single-shot measurement of spin qubit states. We note that, because of charging effects, the resonant charge tunnelling is sequential, that is, only one charge at a time can traverse the barrier by passing through the dopant level. Therefore, care must be taken to ensure that the transparency of the tunnel barrier is sufficient to yield a measurable current. We aim at tunnelling times ~100 ns corresponding to currents of ~1 pA. The drawing in FIG. 2(c) refers to the case where the dopant atom is a donor, and the charge carriers are electrons: the energy landscape should be mirrored in the case of acceptor atoms and holes.

Demonstration of Local Electron Spin Resonance (EDR) on Dopants

The coherent manipulation of the quantum state of a spin qubit requires the application of microwave fields, with a frequency matching the Zeeman splitting of the spin states. The ability to perform local ESR on a small number of dopants [6] has recently been demonstrated, by fabricating a MOS structure 50 where the top gate 52 has the double function of: (i) inducing a GICL in the MOSFET channel; and (ii) supplying the microwave field, see FIG. 3(a). For the latter purpose, the gate 52 is shaped as a coplanar transmission line, terminated by a short circuit. A microwave capacitor allows application of a microwave excitation to the line, in addition to the DC bias needed to induce the GICL. This arrangement yields maximum magnetic field in the channel of the MOSFET, and zero (microwave) electric field.

The absence of microwave electric field in the sensitive region is crucial to guarantee the proper operation of charge-sensing devices. Because there is no resonant structure, this ESR line can be used over an extremely wide frequency range (~10 MHz to ~50 GHz).

Figure 3B:
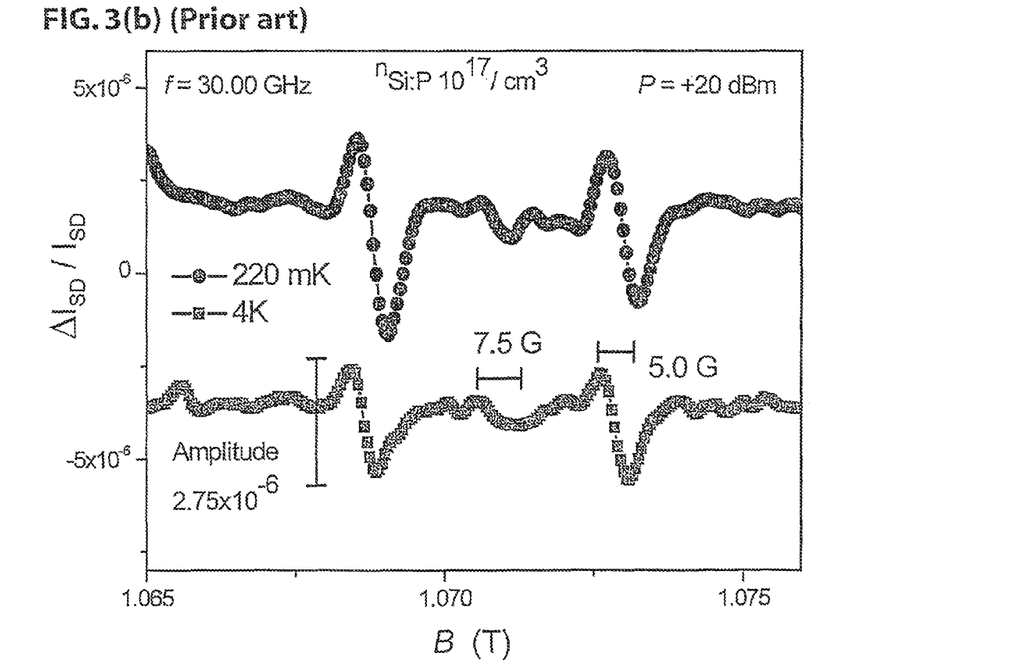
FIG. 3(b) is a graph showing the effect of resonant microwave absorption of the P donors on the source-drain current, at T=4 K and 220 mK, with an excitation frequency f=30 GHz.

To verify the effectiveness of the local ESR line we have performed an EDMR experiment, where a weak but measurable spin-dependent scattering [12] of the conduction electrons with the P donors in the channel allows continuous monitoring of the electron spin polarization by measuring the conductance of the MOSFET. As shown in FIG. 3(b), we were able to observe all the expected features of the ESR of P donors, and (for the first time) to extend this type of investigation to the millikelvin temperature regime [6]. Notice the ability to resolve the hyperfine-split resonance peaks due to the interaction between the electron spin and the $^{31}$P nucleus. This demonstrates the excellent sensitivity of the design.

The next milestone is the coherent control and readout of the electron or hole spin of a single dopant in silicon. Two methods have been successfully demonstrated in GaAs quantum dots: the spin-to-charge conversion for single-shot readout of the electron spin state [13], and local Electron Spin Resonance (ESR) [14] for the coherent manipulation of the spin state. Apart from demonstrating these in silicon devices, another ingredient that has not yet been finalized is an optimal charge reservoir for spin-dependent tunnelling to- and from- a single dopant. Up until this time, the focus for this ingredient has been directed to nanometer-sized Schottky contacts of platinum silicide.

DISCLOSURE OF THE INVENTION

The invention is an electronic device for the control and readout of the electron or hole spin of a single dopant atom in silicon, comprising:

A silicon substrate in which there are one or more ohmic contact regions.

An insulating region on top of the substrate.

First and second barrier gates spaced apart to isolate a small region of charges to form the island of a Single Electron Transistor (SET).

A third gate overlying both the first and second barrier gates, but insulated from them, the third gate being able to generate a gate-induced charge layer (GICL) in the substrate beneath it.

A fourth gate in close proximity of a single dopant atom, the dopant atom being encapsulated in the substrate outside the region of the GICL but close enough to allow spin-dependent charge tunnelling between the dopant atom and the SET island under the control of the potential of the fourth gate.

Wherein, either the third or fourth gate also serve as an Electron Spin Resonance (ESR) line to control the spin of the single electron or hole of the dopant.

Besides its compactness and elegance, the proposed structure is truly innovative in the idea of using the SET island to provide a charge reservoir for spin detection. The concept of combining the charge reservoir, local ESR and charge sensor in a single MOS device clearly constitutes a great advantage in flexibility for the layout of a planar structure for scalable quantum computing.

It is extremely challenging to design a bulk ESR cavity where the electric field in the sensitive area is small enough not to upset the operation of the SET, so the local ESR line in this device is designed to overcome such difficulty.

The device has the additional advantage of being compatible with the industry MOS technology, where the key materials include silicon and aluminium (and their oxides). It is also compatible with our method for the implantation of single ions to serve as the host for the electron spin qubit for prototype devices.

Additionally, the capability to control the qubit (electron or hole spin) by local ESR means that it is not necessary to Stark-shift the individual dopants to select which one is in resonance with a global microwave field. Therefore, the "A-gates" that were necessary in previously proposed architectures [15], could potentially be eliminated.

In one arrangement the fourth gate provides the ESR line in addition to controlling tunnelling of the charge by its electrostatic potential.

In an alternative arrangement the third gate provides the ESR line in addition to generating the GICL in the substrate. In this case the fourth gate still controls tunnelling of the charge by its electrostatic potential.

In a further aspect the invention is a method for using the electronic device, comprising the steps of:

Manipulating the spin of the dopant charge using controlled microwave pulses to the ESR line.

Generating a gate-induced charge layer (GICL) using the third gate.

Controlling tunnelling of the charge from the dopant atom to the GICLSET island by the electrostatic potential on the fourth gate.

And, controlling the operation of the SET.

The SET island may be defined using the barrier gates. Operation of the SET may be controlled using gates one, two and three.

BRIEF DESCRIPTION OF THE DRAWINGS

The prior art has been described above with reference to the accompanying drawings, in which:

FIG. 1 illustrates a silicon quantum dot device.

FIG. 2(a) is a plan view.

FIG. 2(b) is a cross-section.

FIG. 2(c) is a schematic energy landscape.

FIG. 2(d) is a preliminary measurement showing the conductance peaks obtained by resonant tunnelling of charge through a single dopant atom, and their shift in a magnetic field indicating the Zeeman splitting of the spin levels.

FIG. 3 illustrates an Electrically Detected Magnetic Resonance (EDMR) device.

Examples of the invention will now be described with reference to the accompanying drawings, in which:

FIG. 4 illustrates a first example of the invention.

FIG. 5 illustrates a second example of the invention.

BEST MODES OF THE INVENTION

Figure 4A:
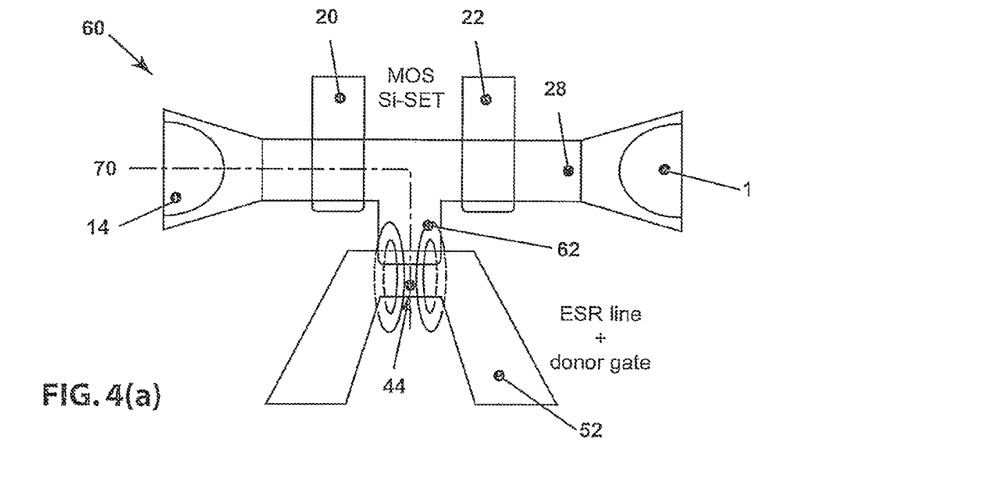
FIG. 4(a) is a plan view of a first device configuration.

Referring now to FIG. 4(a) which shows a complete device 60 for control and readout of the electron or hole spin of a single dopant; remembering that a qubit can be realised in the electron or hole spin of a single dopant atom in silicon. There are a number of techniques available for inserting single donors, for instance those described in U.S. Pat. No. 7,176,066 and U.S. Pat. No. 7,061,008 to the applicant.

The device comprises a Si-SET as shown in FIG. 1(a) and (c), for single-shot detection of charge transfers between an individually placed dopant and a reservoir. In this case the dopant site 44 is in front of the Si-SET island. Also, the top gate 28 has an extended island 62 that protrudes towards the dopant site 44. As a result the GICL 30 in the SET is brought close enough to the implanted dopant 44 to allow (spin-dependent) charge tunnelling between them. The SET island 30 itself is acting as a reservoir for the spin-dependent charge tunnelling to and from the dopant in addition to its usual role.

An additional metal gate 52 provides a local ESR line, as in FIG. 3, running above the dopant site 44, to apply both an electrostatic potential and a microwave magnetic field. Gate 52 therefore provides both the local microwave excitation and the DC bias to lift the energy of the dopant state. It should be appreciated that the extended island 62 does not need to overlay the ESR line 52 for the device to operate.

Control and Readout of a Single Electron or Hole Spin

Figure 4B:
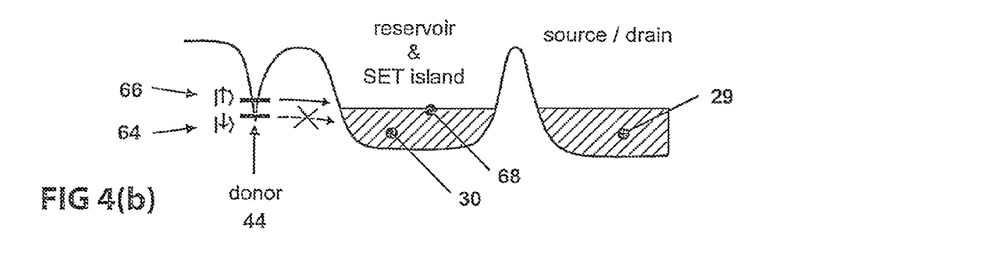
FIG. 4(b) is a graph of the energy landscape of the device.

The electrostatic potential on the ESR line 52 is used to shift the Zeeman-split electron or hole spin levels 64 and 66 with respect to the Fermi level of the reservoir 68. As shown in FIG. 4(b), a spin-to-charge conversion is obtained when the reservoir Fermi level is halfway between the ground (spin-down) and excited (spin-up) electron or hole spin states [13]. The drawing in FIG. 4(b) (and FIG. 5(b) below) refers to the case where the device is implemented using donor atoms, and electrons as charge carriers: the energy landscape should be mirrored in the case of acceptor atoms and holes.

Since the role of reservoir 30 is played here by the SET island, its carriers density of states is not a continuum (as in a bulk metal), but shows discrete levels whose spacing depends on the size and electrostatic potential of the island. The condition to achieve spin-dependent tunnelling between dopant and reservoir is still met as long as the Zeeman splitting of the electron or hole spin states 64 and 66, induced by the external magnetic field, is much larger than the level spacing in the island. In addition, the precise energy level at which tunnelling can occur will also depend on the charging energy of the island. Both these subtle aspects are omitted in the sketch in FIG. 4(b) for simplicity The single-shot detection of charge transfer is equivalent to the projective measurement of the qubit state. Since the charge tunnels directly onto the SET island, the magnitude of the charge transfer signal is expected to be very large, of the order of 10% of an electron, which is easily detectable in single shot by our SETs. The tunnelling time between dopant and reservoir needs to be longer than the measurement time, ~1 μs, requiring a less transparent barrier than used in the transport experiment of FIG. 2(c).

Figure 4C:
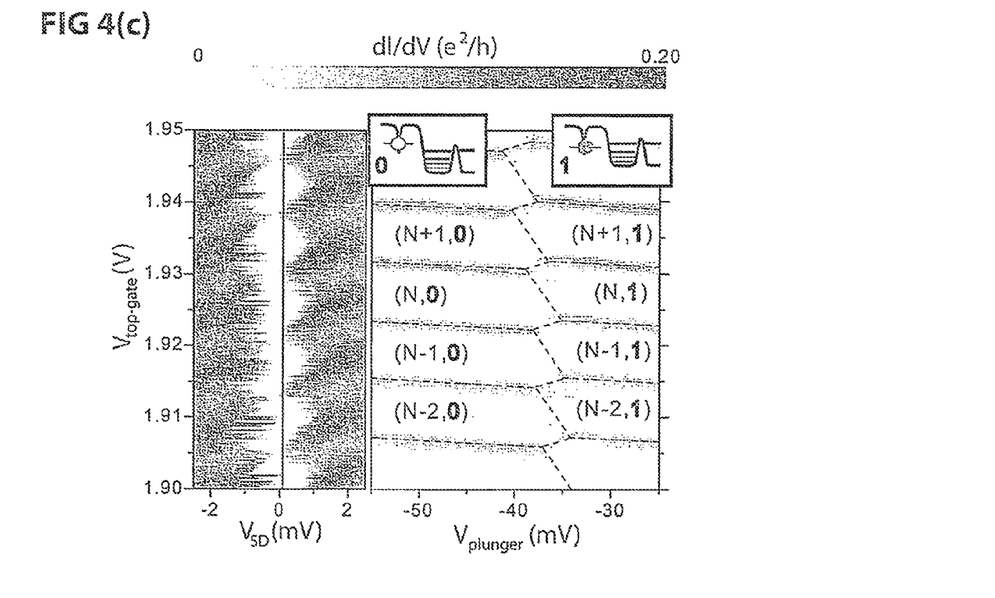
FIG. 4(c) is a preliminary measurement showing the effect of the tunnelling of a single charge between the dopant atom and the SET island.
Figure 4D:
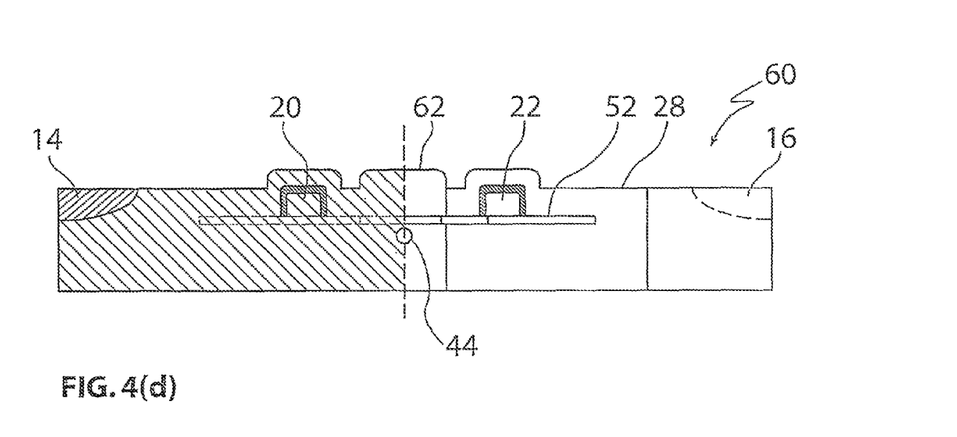
FIG. 4(d) is a schematic cross-section of the device of FIG. 4(a).

FIG. 4(c) shows a preliminary experiment where the change in SET conductance as a consequence of a charge transfer between dopant atom and SET is demonstrated. The current through the SET shows periodic peaks as a function of $V_{topgate}$. By changing $V_{plunger}$, the point 80 is reached where an electron tunnels from the SET island into the empty donor, causing a large shift in the conductance pattern of the SET.

The coherent manipulation of the qubit state will be achieved by applying controlled microwave pulses to the ESR line 52, which induce Rabi oscillation of the spin state [14].

Because of the proximity of the dopant 44 to the SET, it is essential that no electric component of the microwave field is present in the sensitive area. The local ESR technique with short-circuit termination of the line is designed to achieve this goal.

FIG. 4(b) is a graph of the energy landscape along the dash-dotted line 70 shown in panel (a). (Note that the graph is laterally inverted with respect to the device layout). The spin on the dopant electron or hole is initialized using the controlled microwave pulses to the ESR line 52. Tunnelling of the charge from the dopant 44 to the GICL 30 is controlled by the electrostatic potential 72 on the ESR line 52, which has the strongest coupling to the dopant. The influence of the other three gates on the dopant energy levels, although nonzero, is weaker than that of the ESR line, which acts here as fourth gate. The conductance of the SET between source and drain 14/16 is controlled by the barrier gates 20/22, the top gate 28 and the presence or absence of a charge on the dopant 44.

Figure 5A:
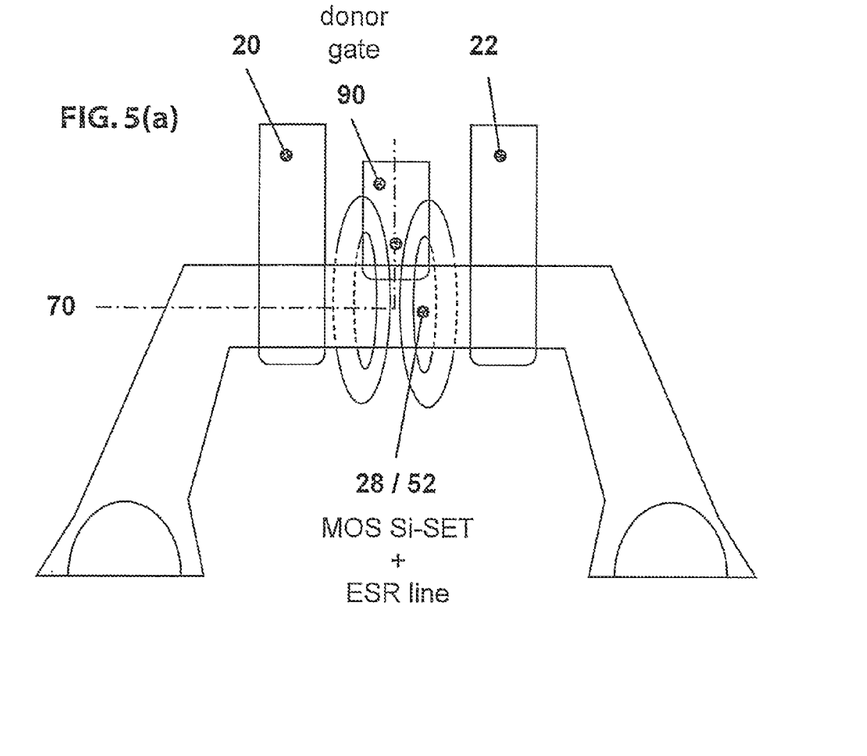
FIG. 5(a) is a plan view of a first device configuration.
Figure 5B:
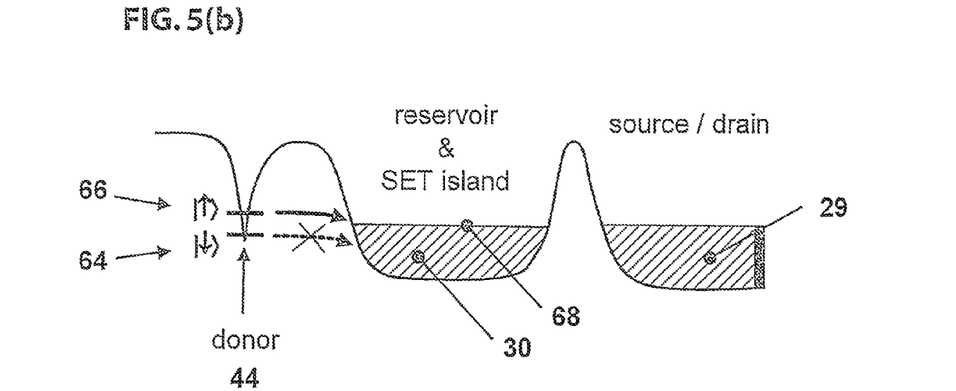
FIG. 5(b) is a graph of the energy landscape of the device.

Referring now to FIG. 5, an alternative configuration for the device will be explained. In this configuration the top gate of the SET 28/52 is shaped to provide the ESR line 52 as well as the Si-SET top gate 28 functionality. The two barrier gates 20 and 22 remain the same, and the dopant site is underneath an additional gate 90 in proximity of the GICL 30. Gate 90 acts as fourth gate by providing the electrostatic potential to control the tunnelling of the charge from the dopant 44 to the GICL 30.

In either case there are a variety of different methods available for reading out the state of a SET coupled to an individual phosphorus donor:

First, the resistance of the SET can be deduced by measuring the power reflected by a resonant tank circuit formed by the SET, its capacitance to ground and an additional inductor. Using this technique the limiting bandwidth, typically 10 MHz, is given by the Q-factor of the resonator. Maximum signal to noise ratio is obtained when the excitation amplitude is comparable to the SET charging energy. As a result, fast readout is possible, but there is a restriction on carrier power for high-fidelity spin readout [17].

Second, the drain of the SET can be connected to a low-noise current preamplifier (I →V converter) at room temperature. This is a very simple method but it imposes a noise-bandwidth tradeoff, since the capacitance of the connecting cable with the input resistance of the preamplifier creates an RC-low pass filter. As a result performance is good down to ~100 μs but it is difficult to measure beyond 10 μs.

A solution to this limitation is to install a buffer stage at low temperature close to the device, for instance a High Electron Mobility Transistor (HEMT) operating a 1 K can be AC coupled to the preamplifier. With this arrangement measurement times down to <1 μs are possible, but there may be back-action between the HEMT and the SET, as well as heating and noise problems [18], [19].

Perhaps an optimal solution involves the use of a low temperature comparator. This takes advantage of the digital operation of the SET in its response to transfer of an electron; its output jumps between zero and maximum conductance. The comparator compares SET current to a reference value to yield the charge, and therefore the spin state of the donor. Such a digital comparator can be built in a CMOS technology compatible with low temperature operation, and the SET and comparator could be built on the same chip, eliminating capacitance problems. Readout times could be as fast as 1 ns, with the additional advantage that the readout circuitry can be integrated on the same silicon chip that hosts the qubit device [20].

Scalable QC Architecture and CTAP

Figure 6:
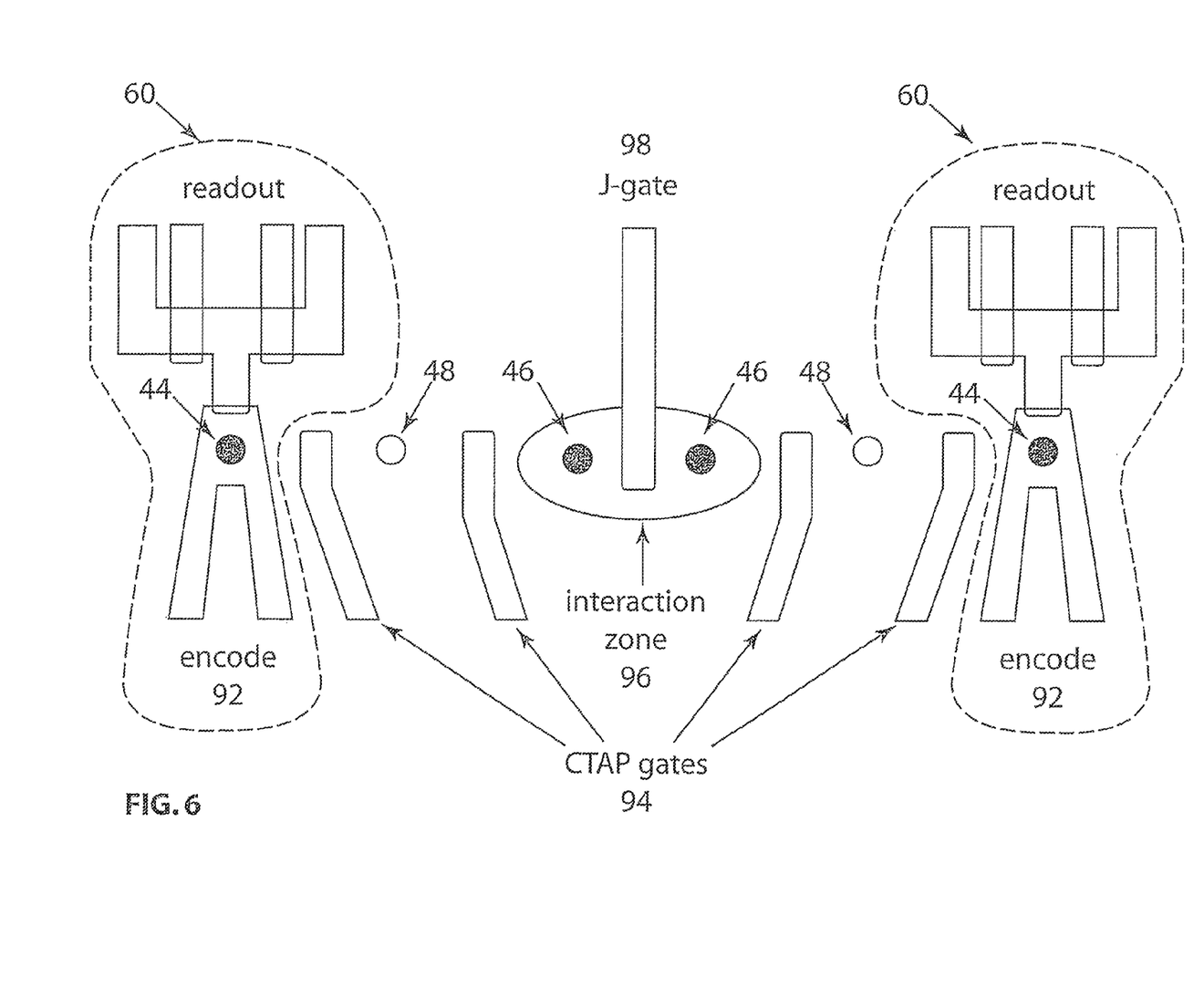
FIG. 6 is a plan view of a scheme of the architecture for logic gates in silicon for a 2× CTAP3 configuration.

The new MOS-compatible spin qubit device configuration of FIGS. 4 and 5 will fit in a 2D scalable single-dopant-based silicon quantum computer architecture [4], where charges are shuttled using Coherent Transport by Adiabatic Passage (CTAP) [16]. FIG. 6 illustrates the scheme of the architecture for logic gates in silicon for a 2×CTAP3 configuration including two of the circuits 60 from FIG. 4 for the readout operations.

The qubits are initialized at the dopants 44 at the ends of the chain, where the encoding 92 of the qubit states is performed. Then the CTAP gates 94 are activated to shuttle the charges to the inner dopants 46 in the interaction zone 96. The ionized dopants 48 are required for the CTAP sequence and remain unoccupied at all times. The CTAP chain can be made longer (CTAP5, 7, . . .) by adding extra ionized dopants 48, without the need for extra CTAP gates 94. The "J-gate" 98 tunes the exchange interaction to perform 2-qubit logic gates. Finally, another CTAP sequence brings the charges back to the ends of the chain, where the spin state is measured by the SETs 60 via the spin-to-charge conversion method.

Figure 7:
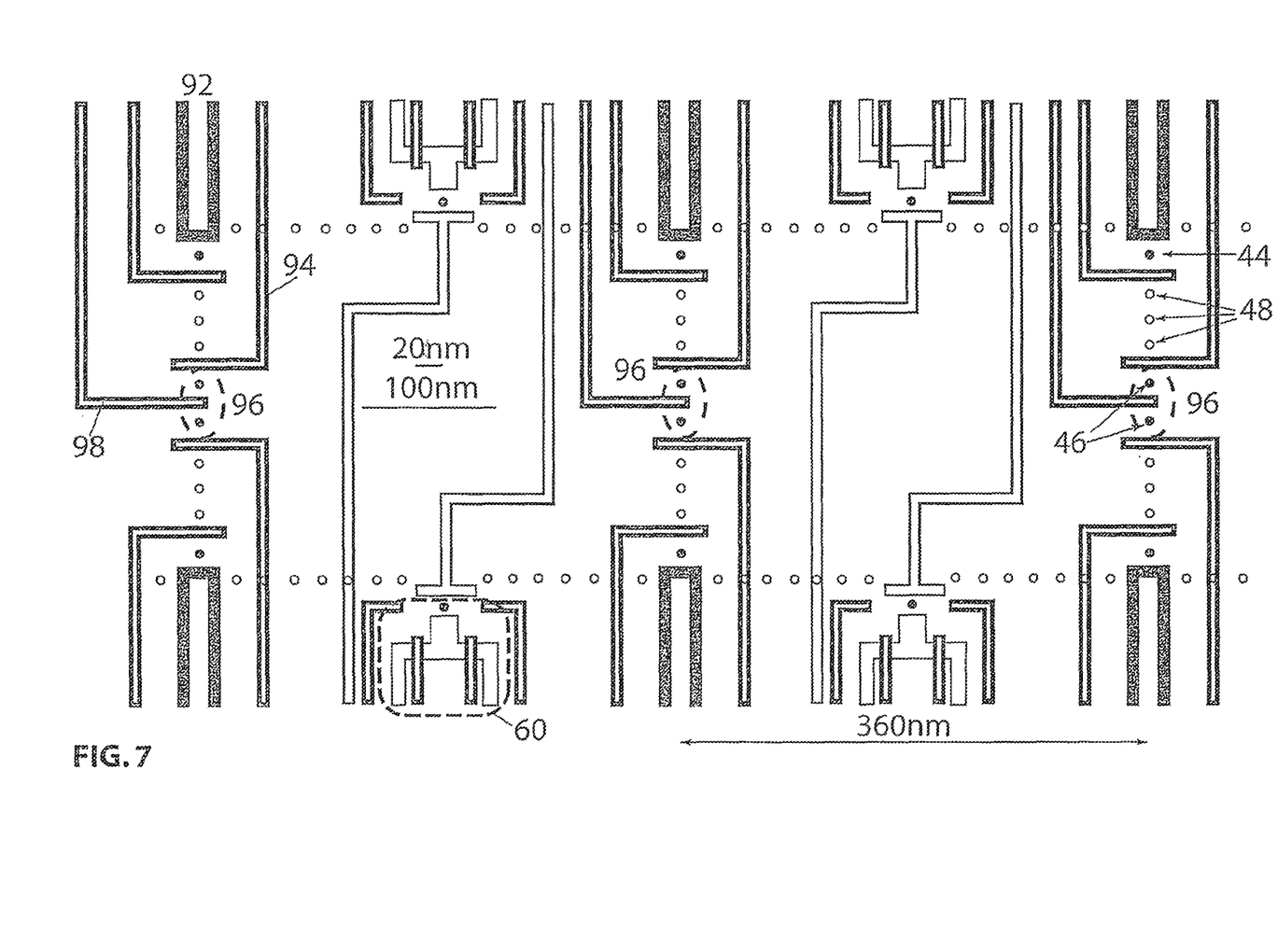
FIG. 7 is a plan view illustrating a scaled up version of the architecture showing many of the logic gates.

FIG. 7 shows how the arrangement of FIG. 6 is used in a scaled up circuit with three interaction zones 96. Incorporation of the combined ESR-reservoir-SET device is also possible and will further streamline the architecture. In FIG. 7, the local ESR control and SET-reservoir detection are placed at distinct locations. The flexibility of the combined ESR-reservoir-SET allows for the architecture to be streamlined further.

Although the invention has been described with reference to a particular example, it should be appreciated that it could be exemplified in many other forms and in combination with other features not mentioned above. For instance, the techniques described in our copending application filed on 6 Feb. 2008 could be employed in the fabrication of this device.

References

The following references are incorporated herein by reference:

[1] D. N. Jamieson, C. Yang, T. Hopf, S. M. Hearne, C. I. Pakes, S. Prawer, M. Mitic, E. Gauja, S. E. Andresen, F. E. Hudson, A. S. Dzurak, and R. G. Clark, Appl. Phys. Lett. 86, 202101 (2005).

[2] T. M. Buehler, D. J. Reilly, R. P. Starrett, N. A. Court, A. R. Hamilton, A. S. Dzurak, and R. G. Clark, J. Appl. Phys. 96, 4508 (2004).

[3] S. E. S. Andresen, R. Brenner, C. J. Wellard, C. Yang, T. Hopf, C. C. Escott, R. G. Clark, A. S. Dzurak, D. N. Jamieson, and L. C. L. Hollenberg, Nano Lett. 7, 2000 (2007).

[4] L. C. L. Hollenberg, A. D. Greentree, A. G. Fowler, and C. J. Wellard, Phys. Rev. B 74, 045311 (2006).

[5] A. M. Stephens, A. G. Fowler, and L. C. L. Hollenberg, Quant. Inf. Comp. 8, 330 (2008).

[6] L. H Willems van Beveren, H. Huebl, R. G. Clark et al., in preparation.

[7] S. J. Angus, A. J. Ferguson, A. S. Dzurak, and R. G. Clark, Nano Lett. 7, 2051 (2007).

[8] S. J. Angus, A. J. Ferguson, A. S. Dzurak, and R. G. Clark, Appl. Phys. Lett., in press.

[9] W. H. Huber, S. B. Martin, and N. M. Zimmerman, in the Proceedings of the 1$^{st}$ international conference on Experimental Implementation of Quantum Computation, Rinton Press Inc. (2001).

[10] H. Sellier, G. P. Lansbergen, J. Caro, S. Rogge, N. Collaert, I. Ferain, M. Jurczak, and S. Biesemans, Phys. Rev. Lett. 97, 206805 (2006).

[11] L. E. Calvet, R. G. Wheeler, and M. A. Reed, Phys. Rev. Lett. 98, 096805 (2007).

[12] R. N. Ghosh and R. H. Silsbee, Phys. Rev. B 46, 12508 (1992).

[13] J. M. Elzerman, R. Hanson, L. H. Willems van Beveren, B. Witkamp, L. M. K. Vandersypen, and L. P. Kouwenhoven, Nature 430, 431 (2004).

[14] F. H. L. Koppens, C. Buizert, K. J. Tielrooij, I. T. Vink, K. C. Nowack, T. Meunier, L. P. Kouwenhoven, and L. M. K. Vandersypen, Nature 442, 776 (2006).

[15] C. D. Hill, L. C. L. Hollenberg, A. G. Fowler, C. J. Wellard, A. D. Greentree, and H.-S. Goan, Phys. Rev. B 72, 045350 (2005).

[16] A. D. Greentree, J. H. Cole, A. R. Hamilton, and L. C. L. Hollenberg, Phys. Rev. B 70, 235317 (2004).

[17] S. J. Angus, A. J. Ferguson, A. S. Dzurak, and R. G. Clark, Appl. Phys. Lett. 92, 112103 (2008).

[18] I. T. Vink, T. Nooitgedagt, R. N. Schouten, L. M. K. Vandersypen, and W. Wegscheider, Appl. Phys Lett. 91, 113512 (2007).

[19] C. H. Yang, T. H. Chang, M. J. Yang, and W. J. Moore, Rev. Sci. Instr. 73, 2713 (2002).

[20] T. M. Gurrieri, M. S. Carroll, M. P. Lilly, and J. E. Levy, DOI: 10.1109/NANO.2008.183 (8$^{th}$ IEEE conference on Nanotechnology)

The invention claimed is:

1. An electronic device for control and readout of electron or hole spin of a single dopant atom in silicon, comprising:
a silicon substrate in which there are one or more ohmic contact regions;
an insulating region on top of the substrate;
first and second spaced-apart barrier gates on top of the insulating region;
an island of a Single Electron Transistor (SET) in the substrate beneath the first and second spaced-apart barrier gates defined by the barrier gates;
a third gate overlying both the first and second barrier gates, but insulated from them and the SET is controlled by the first, second and third gates;
a gate-induced charge layer (GICL) in the substrate beneath the third gate;
wherein the single dopant atom is encapsulated in the substrate outside the region of the GICL, and a fourth gate is in close proximity to the single dopant atom;
and wherein the device further comprises a fourth gate induced intermittent spin-dependent charge tunnel between the dopant atom and the SET island;
and a third or fourth gate induced Electron Spin Resonance (ESR) line in the vicinity of either the third or fourth gate, respectively and manipulating the spin of the electron or hole spin of the single dopant atom.

2. An electronic device for the control and readout of the electron or hole spin of a single dopant atom in silicon, according to claim 1, wherein the fourth gate provides the ESR line in addition to controlling tunneling of the charge by its electrostatic potential.

3. An electronic device for the control and readout of the electron or hole spin of a single dopant atom in silicon, according to claim 1, wherein the third gate provides the ESR line in addition to generating the GICL in the substrate.

4. An electronic device for the control and readout of the electron or hole spin of a single dopant atom in silicon, according to claim 3, wherein the fourth gate controls tunneling of the charge by its electrostatic potential.

5. An electronic device for the control and readout of the electron or hole spin of a single dopant atom in silicon, according to claim 1, in combination with other similar devices where charges are shuttled using coherent transport by adiabatic fast passage between them.

* * * * *